(12) United States Patent
Mortensen et al.

(10) Patent No.: US 12,291,453 B2
(45) Date of Patent: *May 6, 2025

(54) METHANE RICH GAS UPGRADING TO METHANOL

(71) Applicant: HALDOR TOPSØE A/S, Kgs. Lyngby (DK)

(72) Inventors: Peter Mølgaard Mortensen, Roskilde (DK); John Bøgild Hansen, Humlebæk (DK); Kim Aasberg-Petersen, Allerød (DK); Charlotte Stub Nielsen, Holte (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 399 days.

This patent is subject to a terminal disclaimer.

(21) Appl. No.: 17/616,926

(22) PCT Filed: Jun. 4, 2020

(86) PCT No.: PCT/EP2020/065438
§ 371 (c)(1),
(2) Date: Dec. 6, 2021

(87) PCT Pub. No.: WO2020/254116
PCT Pub. Date: Dec. 24, 2020

(65) Prior Publication Data
US 2022/0306467 A1   Sep. 29, 2022

(30) Foreign Application Priority Data

Jun. 18, 2019 (DK) .......................... PA 2019 00735
Jul. 15, 2019 (DK) .......................... PA 2019 00877

(51) Int. Cl.
*C01B 3/40* (2006.01)
*C01B 3/38* (2006.01)
(Continued)

(52) U.S. Cl.
CPC ............... *C01B 3/40* (2013.01); *C01B 3/384* (2013.01); *C07C 29/1518* (2013.01);
(Continued)

(58) Field of Classification Search
CPC ... C01B 3/40; C01B 3/384; C01B 2203/1241; C01B 2203/1258; C01B 2203/1294;
(Continued)

(56) References Cited

U.S. PATENT DOCUMENTS

| 4,946,477 A | 8/1990 | Perka et al. |
| 5,019,356 A | 5/1991 | Silberring |

(Continued)

FOREIGN PATENT DOCUMENTS

| AU | 2011333473 B2 | 11/2015 |
| CN | 101437751 A | 5/2009 |

(Continued)

OTHER PUBLICATIONS

International Preliminary Report on Patentability received for PCT Patent Application No. PCT/EP20/065438, mailed on Dec. 30, 2021, 9 pages.

(Continued)

*Primary Examiner* — Jafar F Parsa
(74) *Attorney, Agent, or Firm* — Boone IP Law

(57) ABSTRACT

A method for upgrading a hydrocarbon feed gas to methanol, including the steps of: providing a hydrocarbon feed gas; optionally, purifying the hydrocarbon feed gas in a gas purification unit; optionally, prereforming the hydrocarbon feed gas together with a steam feedstock in a prereforming unit; carrying out steam methane reforming in a reforming reactor heated by means of an electrical power source; providing the synthesis gas to a methanol synthesis unit to provide a product including methanol and an off-gas. Also, a system for upgrading a hydrocarbon feed gas to methanol.

19 Claims, 5 Drawing Sheets

(51) Int. Cl.
*C07C 29/151* (2006.01)
*C07C 29/152* (2006.01)
*C25B 1/042* (2021.01)
*C25B 15/08* (2006.01)

(52) U.S. Cl.
CPC ............ *C07C 29/152* (2013.01); *C25B 1/042* (2021.01); *C25B 15/081* (2021.01); *C01B 2203/0233* (2013.01); *C01B 2203/0405* (2013.01); *C01B 2203/061* (2013.01); *C01B 2203/0827* (2013.01); *C01B 2203/085* (2013.01); *C01B 2203/1017* (2013.01); *C01B 2203/1241* (2013.01); *C01B 2203/1258* (2013.01); *C01B 2203/1294* (2013.01); *C01B 2203/142* (2013.01); *C01B 2203/148* (2013.01); *C01B 2203/1614* (2013.01); *C01B 2203/1628* (2013.01)

(58) Field of Classification Search
CPC ... C07C 29/1518; C07C 29/152; C25B 1/042; C25B 15/081
See application file for complete search history.

(56) References Cited

U.S. PATENT DOCUMENTS

| | | | |
|---|---|---|---|
| 6,048,472 | A | 4/2000 | Nataraj et al. |
| 6,114,400 | A | 9/2000 | Nataraj et al. |
| 6,846,951 | B1 | 1/2005 | Thiebaut |
| 2006/0124445 | A1 | 6/2006 | Labrecque et al. |
| 2007/0254967 | A1 | 11/2007 | West et al. |
| 2012/0025140 | A1 | 2/2012 | Tetzlaff |
| 2012/0115965 | A1 | 5/2012 | Olah et al. |
| 2012/0270119 | A1 | 10/2012 | Raaheim et al. |
| 2015/0129805 | A1 | 5/2015 | Karpenko et al. |
| 2016/0060537 | A1 | 3/2016 | Hsu |
| 2016/0083260 | A1 | 3/2016 | Dahl |
| 2017/0106360 | A1 | 4/2017 | Meriam |
| 2018/0148330 | A1 | 5/2018 | Tamhankar et al. |
| 2018/0258019 | A1 | 9/2018 | Roesch et al. |
| 2019/0337876 | A1 | 11/2019 | Short et al. |

FOREIGN PATENT DOCUMENTS

| | | | |
|---|---|---|---|
| CN | 101730657 | A | 6/2010 |
| CN | 102762493 | A | 10/2012 |
| CN | 104193584 | A | 12/2014 |
| CN | 105209373 | A | 12/2015 |
| CN | 108779050 | A | 11/2018 |
| DE | 102013226126 | A1 | 6/2015 |
| EP | 2650257 | A1 | 10/2013 |
| GB | 2375353 | A | 11/2002 |
| GB | 201522326 | | 2/2016 |
| GB | 2545474 | A | 6/2017 |
| JP | 2015509905 | A | 4/2015 |
| JP | 2017178810 | A | 10/2017 |
| WO | 2017/103679 | A1 | 6/2017 |
| WO | 2018115596 | A1 | 6/2018 |
| WO | 2019110266 | A1 | 6/2019 |
| WO | 2019110268 | A1 | 6/2019 |

OTHER PUBLICATIONS

International Preliminary Report on Patentability received for PCT Patent Application No. PCT/EP2020/065475, mailed on Dec. 30, 2021, 8 pages.
Office Action received for Chinese Patent Application No. 202080044542.2, mailed on Oct. 25, 2023, 14 pages (4 pages of English Translation and 10 pages of Original Document).
Office Action received for Chinese Patent Application No. 202080044555.X, mailed on Nov. 14, 2023, 16 pages (6 pages of English Translation and 10 pages of Original Document).
Danish Search Report mailed on Dec. 12, 2019 in Danish Application No. PA 2019 00735 by Danish Patent and Trademark Office.
Danish Search Report mailed on Dec. 18, 2019 in Danish Application No. PA 2019 00732 by Danish Patent and Trademark Office.
Danish Search Report mailed on Jan. 8, 2020 in Danish Application No. PA 2019 00874 by Danish Patent and Trademark Office.
International Search Report (PCT/ISA/210) with translation and Written Opinion (PCT/ISA/237) mailed on Aug. 21, 2020, by the European Patent Office as the International Searching Authority for International Application No. PCT/EP2020/065438. (13 pages).
International Search Report (PCT/ISA/210) with translation and Written Opinion (PCT/ISA/237) mailed on Jul. 28, 2020, by the European Patent Office as the International Searching Authority for International Application No. PCT/EP2020/065475. (12 pages).

METHANE RICH GAS UPGRADING TO METHANOL

FIELD OF THE INVENTION

Embodiments of the invention generally relate to a method and a system for upgrading methane rich gas to methanol.

BACKGROUND

The classical approach to methanol production involves steam reforming of hydrocarbons and a major associated CO2 emission. As the highly endothermic steam reforming reaction is facilitated in fired reformers using large furnaces operating at temperatures in the vicinity of 1000° C., the process economy is heavily favored by economy of scale to enable high process efficiency and integrated waste heat management. Such plants are therefore difficult to scale down economically due to the integrated design and high upfront capital investment. Consequently, the typical methanol plants exceed production capacities of 2000 MT/day.

It is an object of the invention to provide a method and system for converting methane rich gas to methanol. It is a further object of the invention to provide a sustainable method and system for converting methane rich gas to methanol.

SUMMARY OF THE INVENTION

The invention relates to sustainable production of methanol from a hydrocarbon feed gas by applying the electrically heated steam methane reformer (eSMR) technology that will allow for a practical zero-emission chemical plant with complete or substantially complete carbon utilization.

Embodiments of the invention generally relate to a method and system for upgrading a hydrocarbon feed gas to methanol. This hydrocarbon feed gas could be natural gas, town gas, shale gas or biogas. In the following biogas will be used as example, which has a natural content of $CO_2$.

The term "biogas" in connection with the present invention means a gas with the following composition:

| Compound | Formula | % |
| --- | --- | --- |
| Methane | CH4 | 50-75 |
| Carbon dioxide | CO2 | 25-50 |
| Nitrogen | N2 | 0-10 |
| Hydrogen | H2 | 0-1 |
| Oxygen | O2 | 0-1 |

A first aspect of the invention relates to a method for upgrading hydrocarbon feed gas to methanol, comprising the steps of:
a) providing a hydrocarbon feed gas,
b1) optionally, providing $CO_2$ to the process
b2) optionally, purifying the hydrocarbon feed gas in a gas purification unit,
b3) optionally, prereforming the hydrocarbon feed gas together with a steam feedstock in a prereforming unit,
c) carrying out steam methane reforming in a reforming reactor with a comprising a pressure shell housing a structured catalyst arranged to catalyze steam reforming of said hydrocarbon feed gas, said structured catalyst comprising a macroscopic structure of an electrically conductive material, said macroscopic structure supporting a ceramic coating, where said ceramic coating supports a catalytically active material; said steam methane reforming comprising the following steps:
c1) supplying said hydrocarbon feed gas to the reforming reactor,
c2) allowing the hydrocarbon feed gas to undergo steam reforming reaction over the structured catalyst and outletting a synthesis gas from the reforming reactor, and
c3) supplying electrical power via electrical conductors connecting an electrical power supply placed outside said pressure shell to said structured catalyst, allowing an electrical current to run through said macroscopic structure material, thereby heating at least part of the structured catalyst to a temperature of at least 500° C.,
d) providing at least part of the synthesis gas of step c2) to a methanol synthesis unit to provide a product comprising methanol and an off-gas.

The step b1) of providing $CO_2$ to the process is also understood to cover the cases where $CO_2$ is present in the hydrocarbon feed gas. Moreover, step d) of providing at least part of the synthesis gas to the methanol synthesis unit also covers the case, where water is removed from the synthesis gas prior to leading the synthesis gas, in this case a dry or drier synthesis gas, to the methanol synthesis unit. The synthesis gas obtained in step c) may e.g. be cooled to a temperature below the dew point of the gas and be separated to a liquid phase comprising water and a gas phase comprising the dry synthesis gas, upstream the methanol synthesis unit.

The traditional methanol production involves steam reforming of hydrocarbons followed by a methanol synthesis unit; this provides for a major associated $CO_2$ emission.

Moreover, this traditional methanol production gives little opportunity for energy storage and no debottlenecking of the energy fluctuations associated with renewable electricity. As the highly endothermic steam reforming reaction is facilitated in fired reformers using large furnaces operating at temperatures in the vicinity of 1000° C., the process economy is heavily favored by economy of scale to enable high process efficiency and integrated waste heat management. Such plants are therefore difficult to scale down economically due to the integrated design and high upfront capital investment. Consequently, the typical methanol plants exceed production capacities of 2000 MT/day.

An alternative route to methanol production is electrolysis of water for hydrogen production mixed with $CO_2$ for methanol production. This concept is proven and largescale operation has already been performed with a capacity of 11 MT/day in Iceland, using alkaline electrolysis for hydrogen production. However, such plants are limited to locations with high availability of electricity, low electricity prices, and/or readily available high-grade $CO_2$. Especially $CO_2$ is a sparse resource and is typically financially unattractive to utilize. Overall, the process economy of the electrolysis-driven frontend to a methanol plant remains very expensive compared with the classical steam reforming approach, because $CO_2$-separation/purification combined with water electrolysis and subsequent compression has a very high net energy use, overall giving methanol production prices 4-6 higher than equivalent fossil fuels. The use of only $CO_2$ and hydrogen as make-up gas to the methanol synthesis also requires more catalyst inventory and reactor size, etc. due to the low reactivity of the gas. The application of co-electrolysis by solid oxide electrolysis cells (SOEC) could produce a more efficient and smaller methanol synthesis, but this approach is currently only at laboratory scale. In addition, electrolysis in general also has a high upfront capital investment presently, which only makes the process economy more challenged.

By the term "methanol synthesis unit" is understood one or several reactors configured to convert a synthesis gas into methanol. Such reactors can for example be a boiling water reactor, an adiabatic reactor, a condensing methanol reactor or a gas-cooled reactor. Moreover, these reactors could be many parallel reactor shells and sequential reactor shells with intermediate heat exchange and/or product condensation. It is understood that the methanol synthesis unit also contains equipment for recycling and pressurizing feed to the methanol reactor(s). The term "hydrocarbon feed gas" is meant to cover both the hydrocarbon feed gas as well as a purified hydrocarbon feed gas, a prereformed hydrocarbon feed gas and a hydrocarbon feed gas with added steam and/or with added hydrogen and/or with added off-gas from the methanol synthesis unit. All constituents of the hydrocarbon feed gas are pressurized, either separately or jointly, upstream the reforming reactor. Typically, steam is pressurized separately; whilst the other constituents of the hydrocarbon feed gas may be pressurized jointly. The pressure(s) of the constituents of the hydrocarbon feed gas is/are chosen so that the pressure within the reforming reactor lies between 5 to 100 bar, preferably between 20 and 40 bar, or preferably between 70 and 90 bar.

In an embodiment, the electrical power supplied has been generated at least partly by means of renewable energy sources. Full utilization of methanol as an energy vector cannot be realized unless a more optimal production route is introduced. For this purpose, the method and plant of the invention uses renewable electricity to increase the energy value of hydrocarbon feed gas (such as methane) into methanol. The electrically heated steam methane reformer (eSMR) is a very compact steam reforming reactor, resulting in a lower capital investment than classical steam reforming equipment. The hydrocarbons in the hydrocarbon feed gas are preferably mainly methane; however, the hydrocarbon feed gas may also comprise small amounts of higher hydrocarbons. The hydrocarbon feed gas can come from any methane-containing source such as biogas or natural gas, but because heating is facilitated by electricity, it will be an improvement over the existing fired reformer by saving the direct $CO_2$ emissions. In addition, an excellent synergy exists with a biogas feedstock that will allow for practically full conversion of all carbon in the biogas to methanol.

In an embodiment, wherein an electrolysis unit is used to generate a hydrogen rich stream from a water feedstock and where the hydrogen rich stream is added to the synthesis gas to balance the module M of the synthesis gas to be in the range of 1.5 to 2.5. Preferably, the module M of the synthesis gas is balanced to be in the range of 1.95 to 2.1. The module M of a synthesis gas is $$M = \frac{H_2 - CO_2}{CO + CO_2}.$$

In an embodiment, the electrolysis unit is a solid oxide electrolysis cell unit and the water feedstock is in the form of steam produced from other processes of the method.

Steam is e.g. generated in the methanol synthesis unit or waste heat boiler of the system for upgrading hydrocarbon feed gas to methanol.

In an embodiment, a membrane unit is included in the methanol synthesis unit to extract at least part of the carbon containing molecules, such as CO and $CO_2$, from the off-gas and return the at least part of the carbon containing molecules of the off-gas to the synthesis gas to balance the module M of the synthesis gas to be in the range of 1.5 to 2.5. Preferably, the module M of the synthesis gas is balanced to be in the range of 1.95 to 2.1. Again, the module M is defined as:

$$M = \frac{H_2 - CO_2}{CO + CO_2}.$$

In an embodiment, a combination of steam superheating and steam generation is integrated in the waste heat recovery of the hot synthesis gas product from the reforming reactor, and the superheated steam is used as steam feedstock in step c) of the method for upgrading a hydrocarbon feed gas to methanol.

In an embodiment, the pressure of the gas inside the reforming reactor is between 20 and 100 bar, preferably between 50 and 90 bar.

In an embodiment, the temperature of the gas exiting the reforming reactor is between 900 and 1150° C.

In an embodiment, the space velocity evaluated as flow of gas relative to the geometric surface area of the structured catalyst is between 0.6 and 60 $Nm^3/m^2/h$ and/or the flow of gas relative to the occupied volume of the structured catalyst is between 700 $Nm^3/m^3/h$ and 70000 $Nm^3/m^3/h$. Preferably, the flow of gas relative to the occupied volume of the structured catalyst is between 7000 $Nm^3/m^3/h$ and 10000 $Nm^3/m^3/h$.

In an embodiment, the plot area of the reforming reactor is between 0.4 $m^2$ and 4 $m^2$. Preferably, the plot area is between 0.5 and 1 $m^2$. Here the term "plot area" is meant to be equivalent to "ground area", viz. the area of land that the reforming reactor will take up when installed.

In an embodiment, the production of methanol is regulated according to availability of renewable energy.

In an embodiment, the method further comprises the step of upgrading the raw methanol to fuel grade methanol.

In an embodiment, the methanol is upgraded to chemical grade methanol.

In an embodiment, the method further comprises the step of using at least part of the methanol of step d) to a system for producing transportation fuel. In particular, the methanol is used as feedstock in a system for methanol to gasoline synthesis.

In an embodiment, between 80% and 100% of the carbon in the hydrocarbon feed gas is converted into methanol. This means than between 80% and 100% of the carbon atoms in the hydrocarbon feed gas are converted into carbon bounded in methanol molecules during the method of the invention.

In an embodiment, the hydrocarbon feed gas amounts to 500 $Nm^3/h$ to 8000 $Nm^3/h$.

In an embodiment of the invention, the hydrocarbon feed gas is biogas. In a particular embodiment, wherein the hydrocarbon feed gas is biogas, a part of the off-gas produced in step d) is recycled to a biogas production facility for producing the biogas to be upgraded in the method of the invention. As said off-gas typically has a high content of hydrogen, this hydrogen can be used in a biogas production facility, i.e. a fermentation plant, where it can react with carbon oxides to produce methane. Effectively, this means that in a process constellation where an amount of hydrogen rich off-gas is recycled to the biogas production facility, the produced biogas will have higher $CH_4/CO_2$ ratio than a biogas produced in a biogas production facility with no recycling of said hydrogen-rich off-gas.

Another aspect of the invention, relates to a system for upgrading a hydrocarbon feed gas to methanol, comprising:
an optional gas purification unit,
an optional prereforming unit,
a reforming reactor with a comprising a pressure shell housing a structured catalyst arranged to catalyse steam reforming of said hydrocarbon feed gas, said structured catalyst comprising a macroscopic structure of an electrically conductive material, said macroscopic structure supporting a ceramic coating, where said ceramic coating supports a catalytically active material; wherein the reforming reactor moreover comprises an electrical power supply placed outside said pressure shell and electrical conductors connecting said electrical power supply to said structured catalyst, allowing an electrical current to run through said macroscopic structure material to thereby heat at least part of the structured catalyst to a temperature of at least 500° C.,
a methanol synthesis unit arranged to receive a synthesis gas from said reforming reactor and produce a product comprising methanol and an off-gas.

The structured catalyst of the reforming reactor of the system is configured for steam reforming. This reaction takes place according to the following reactions:

$$CH_4 + H_2O \leftrightarrow CO + 3H_2$$

$$CH_4 + 2H_2O \leftrightarrow CO_2 + 4H_2$$

$$CH_4 + CO_2 \leftrightarrow 2CO + 2H_2$$

The structured catalyst is composed a metallic structure, a ceramic phase, and an active phase. The metallic structure may be FeCrAlloy, Alnico, or similar alloys. The ceramic phase may be $Al_2O_3$, $MgAl_2O_3$, $CaAl_2O_3$, $ZrO_2$, or a combination thereof. The catalytically active material may be Ni, Ru, Rh, Ir, or a combination thereof.

In an embodiment, catalyst pellets are loaded on top of, around, inside, or below the structured catalyst of the reforming reactor. The catalyst material for the reaction may be $Ni/Al_2O_3$, $Ni/MgAl_2O_3$, $Ni/CaAl_2O_3$, $Ru/MgAl_2O_3$, or $Rh/MgAl_2O_3$. The catalytically active material may be Ni, Ru, Rh, Ir, or a combination thereof. This can improve the overall gas conversion inside the reforming reactor.

In an embodiment, the macroscopic structure(s) has/have a plurality of parallel channels, a plurality of non-parallel channels and/or a plurality of labyrinthic channels. The channels have walls defining the channels. Several different forms and shapes of the macroscopic structure can be used as long as the surface area of the structured catalyst exposed to the gas is as large as possible. In a preferred embodiment, the macroscopic structure has parallel channels, since such parallel channels render a structured catalyst with a very small pressure drop. In a preferred embodiment, parallel longitudinal channels are skewed in the longitudinal direction of the macroscopic structure. In this way, molecules of the gas flowing through the macroscopic structure will mostly tend to hit a wall inside the channels instead of just flowing straight through a channel without necessarily getting into contact with a wall. The dimension of the channels should be appropriate in order to provide a macroscopic structure with a sufficient resistivity. For example, the channels could be quadratic (as seen in cross section perpendicular to the channels) and have a side length of the squares of between 1 and 3 mm; however, channels having a maximum extent in the cross section of up to about 4 cm are conceivable. Moreover, the thickness of the walls should be small enough to provide a relatively large electrical resistance and large enough to provide sufficient mechanical strength. The walls may e.g. have a thickness of between 0.2 and 2 mm, such as about 0.5 mm, and the ceramic coating supported by the walls has a thickness of between 10 μm and 500 μm, such as between 50 μm and 200 μm, such as 100 μm. In another embodiment, the macroscopic structure of the structured catalyst is cross-corrugated. In general, when the macroscopic structure has parallel channels, the pressure drop from the inlet to the outlet of the reforming reactor system may be reduced considerably compared to a reactor where the catalyst material is in the form of pellets such as a standard SMR.

In an embodiment, the macroscopic structure(s) is/are extruded and sintered structures. Alternatively, the macroscopic structure(s) is/are 3D printed structure(s). A 3D printed structure can be provided with or without subsequent sintering. Extruding or 3D printing a macroscopic structure, and optional subsequent sintering thereof results in a uniformly and coherently shaped macroscopic structure, which can afterwards be coated with the ceramic coating.

Preferably, the macroscopic structure has been manufactured by 3D printing or extrusion of a mixture of powdered metallic particles and a binder to an extruded structure and subsequent sintering of the extruded structure, thereby providing a material with a high geometric surface area per volume. Preferably, the 3D printed extruded structure is sintered in a reducing atmosphere to provide the macroscopic structure. Alternatively, the macroscopic structure is 3D printed a metal additive manufacturing melting process, viz. a 3D printing processes, which do not require subsequent sintering, such as powder bed fusion or direct energy deposition processes. Examples of such powder bed fusion or direct energy deposition processes are laser beam, electron beam or plasma 3D printing processes. As another alternative, the macroscopic structure may have been manufactured as a 3D metal structure by means of a binder-based metal additive manufacturing process, and subsequent sintered in a non-oxidizing atmosphere at a first temperature $T_1$, where $T_1 > 1000°$ C., in order to provide the macroscopic structure.

A ceramic coating, which may contain the catalytically active material, is provided onto the macroscopic structure before a second sintering in an oxidizing atmosphere, in order to form chemical bonds between the ceramic coating and the macroscopic structure. Alternatively, the catalytically active material may be impregnated onto the ceramic coating after the second sintering. When chemical bonds are formed between the ceramic coating and the macroscopic structure, an especially high heat conductivity between the electrically heated macroscopic structure and the catalytically active material supported by the ceramic coating is possible, offering close and nearly direct contact between the heat source and the catalytically active material of the structured catalyst. Due to close proximity between the heat source and the catalytically active material, the heat transfer is effective, so that the structured catalyst can be very efficiently heated. A compact reforming reactor system in terms of gas processing per reforming reactor system volume is thus possible, and therefore the reforming reactor system housing the structured catalyst may be compact. The reforming reactor system of the invention does not need a furnace and this reduces the overall reactor size considerably. Moreover, it is an advantage that the amount of synthesis gas produced in a single pressure shell is increased considerably compared to known tubular steam reformers.

In a standard tubular steam reformer, the amount of synthesis gas produced in a single tube of the tubular steam reformer is up to 500 Nm$^3$/h. In comparison, the reforming reactor of the invention is arranged to produce up to or more than 2000 Nm$^3$/h, e.g. even up to or more than 10000 Nm$^3$/h, within a single pressure shell. This can be done without the presence of O$_2$ in the feed gas and with less than 10% methane in the synthesis gas produced. When a single pressure shell houses catalyst for producing up to 10000 Nm$^3$/h synthesis gas, it is no longer necessary to provide a plurality of pressure shells or means for distributing feed gas to a plurality of such separate pressure shells.

As used herein, the terms "3D print" and "3D printing" is meant to denote a metal additive manufacturing process. Such metal additive manufacturing processes cover 3D printing processes in which material is joined to a structure under computer control to create a three-dimensional object, where the structure is to be solidified, e.g. by sintering, to provide the macroscopic structure. Moreover, such metal additive manufacturing processes cover 3D printing processes, which do not require subsequent sintering, such as powder bed fusion or direct energy deposition processes. Examples of such powder bed fusion or direct energy deposition processes are laser beam, electron beam or plasma 3D printing processes.

Preferably, the catalytically active material is particles having a size from 5 nm to 250 nm. The ceramic coating may for example be an oxide comprising Al, Zr, Mg, Ce and/or Ca. Exemplary coatings are calcium aluminate or a magnesium aluminum spinel. Such a ceramic coating may comprise further elements, such as La, Y, Ti, K or combinations thereof. Preferably, the conductors are made of different materials than the macroscopic structure. The conductors may for example be of iron, nickel, aluminum, copper, silver or an alloy thereof. The ceramic coating is an electrically insulating material and will typically have a thickness in the range of around 100 μm, e.g. about 10-500 μm.

The macroscopic structure is advantageously a coherent or consistently intra-connected material in order to achieve electrical conductivity throughout the macroscopic structure, and thereby achieve thermal conductivity throughout the structured catalyst and in particular providing heating of the a catalytically active material supported by the macroscopic structure. By using the coherent or consistently intra-connected material, it is possible to ensure uniform distribution of current within the macroscopic structure and thus uniform distribution of heat within the structured catalyst. Throughout this text, the term "coherent" is meant to be synonymous to cohesive and thus refer to a material that is consistently intra-connected or consistently coupled. The effect of the structured catalyst being a coherent or consistently intra-connected material is that a control over the connectivity within the material of the structured catalyst and thus the conductivity of the macroscopic structure is obtained. It is to be noted that even if further modifications of the macroscopic structure are carried out, such as provision of slits within parts of the macroscopic structure or the implementation of insulating material within the macroscopic structure, the macroscopic structure is still denoted a coherent or consistently intra-connected material.

In an embodiment, the structured catalyst has electrically insulating parts arranged to increase the current path between the conductors to a length larger than the largest dimension of the structured catalyst. The provision of a current path between the conductors larger than the largest dimension of the structured catalyst may be by provision of electrically insulating parts positioned between the conductors and preventing the current running through some part of the structured catalyst. Such electrically insulating parts are arranged to increase the current path and thus increase the resistance through the structured catalyst. In an embodiment, the at least one electrically insulating part has a length arranged to ensure that the minimum current path between the conductors is larger than the largest dimension of the macroscopic structure.

Non-limiting examples of such insulating parts are cuts, slits, or holes in the structure. Optionally, a solid insulating material such as ceramics in cuts or slits in the structure can be used. In a case where the solid insulating material is a porous ceramic material, the catalytically active material may advantageously be incorporated in the pores, by e.g. impregnation. A solid insulating material within a cut or slit assists in keeping the parts of the structured catalyst on the sides of the cut or slit from each other. As used herein, the term "largest dimension of the structured catalyst" is meant to denote the largest inner dimension of the geometrical form taken up by the structured catalyst. If the structured catalyst is box-formed, the largest dimension would be the diagonal from one corner to the farthest corner, also denoted the space diagonal.

It should be noted that even though the current through the structured catalyst may be arranged to twist or wind its way through the structured catalyst due to the electrically insulating parts arranged to increase the current path, the gas passing through the reforming reactor system is inlet at one end of the reforming reactor system, passes through the structured catalyst once before being outlet from the reforming reactor system. Inert material is advantageously present in relevant gaps between the structured catalyst and the rest of the reforming reactor system to ensure that the gas within the reforming reactor system passes through the structured catalyst and the catalytically active material supported thereby.

In an embodiment, the length of the gas passage through the structured catalyst is less than the length of the passage of current from one conductor through the structured catalyst and to the next conductor. The ratio of the length of the gas passage to the length of the current passage may be less than 0.6, or 0.3, 0.1, or even down to 0.002.

In an embodiment, the structured catalyst has electrically insulating parts arranged to make the current path through the structured catalyst a zigzag path. Here, the terms "zigzag path" and "zigzag route" is meant to denote a path that has corners at variable angles tracing a path from one conductor to another. A zigzag path is for example a path going upwards, turning, and subsequently going downwards. A zigzag path may have many turns, going upwards and subsequently downwards many times through the structured catalyst, even though one turn is enough to make the path a zigzag path.

The following is a detailed description of embodiments of the invention depicted in the accompanying drawings. The embodiments are examples and are in such detail as to clearly communicate the invention. However, the amount of detail offered is not intended to limit the anticipated variations of embodiments; but on the contrary, the intention is to cover all modifications, equivalents, and alternatives falling within the spirit and scope of the present invention as defined by the appended claims.

DETAILED DESCRIPTION OF THE DRAWINGS

Figure 1:
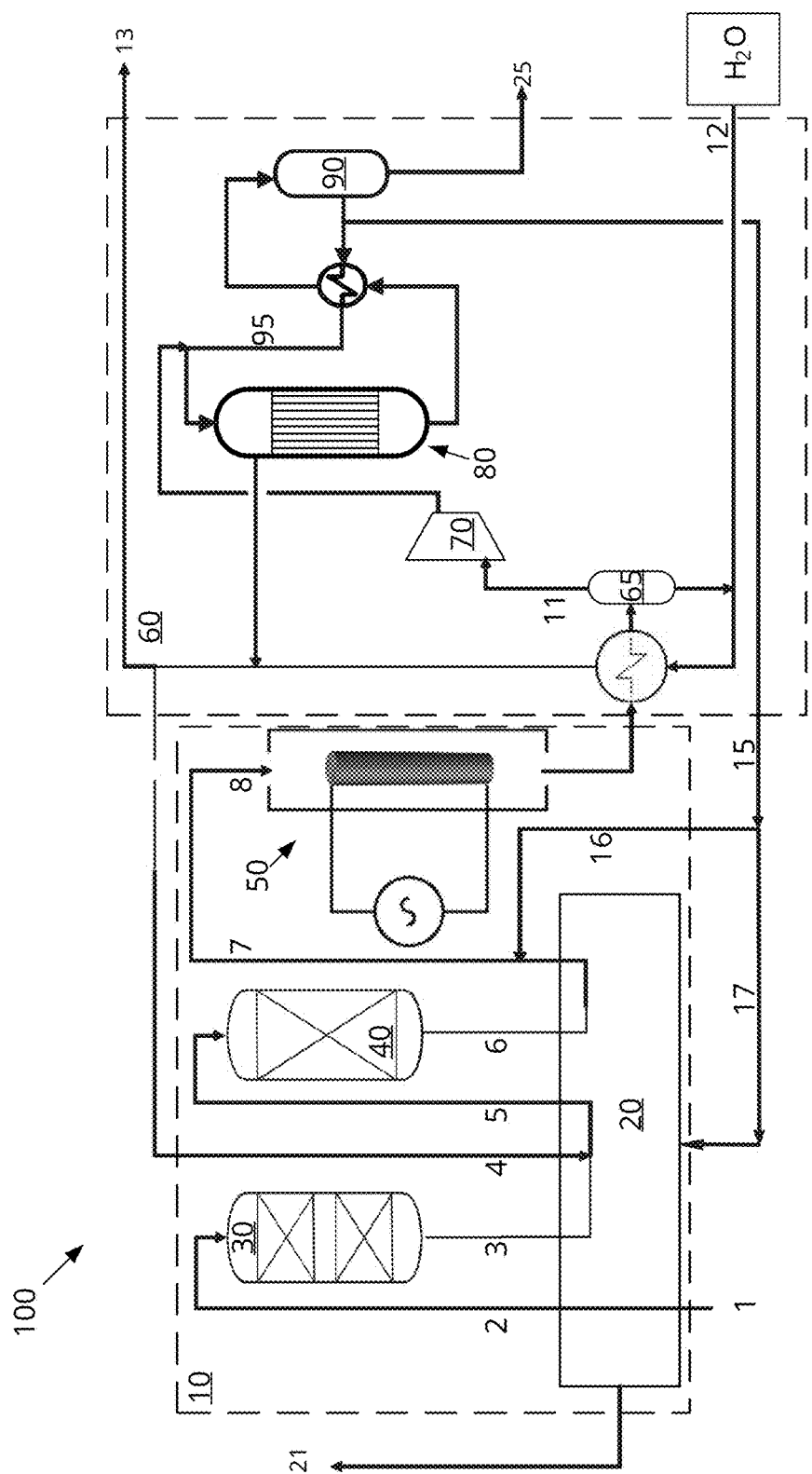
FIG. 1 is a schematic drawing of a system for upgrading a hydrocarbon feed gas to methanol.

FIG. 1 is a schematic drawing of a system 100 for upgrading of hydrocarbon feed gas to methanol. The system is a methanol plant comprising an electrically heated steam methane reformer (eSMR) 50.

The system 100 for upgrading a hydrocarbon feed gas to methanol comprises a reforming section 10 and a methanol section 60. The reforming section 10 comprises a preheating section 20, a purification unit 30, e.g. a desulfurization unit, a prereformer 40 and an eSMR 50. The methanol section comprises a first separator 85, a compressor unit 70, a methanol synthesis unit 80, a second separator 90 as well as heat exchangers. The first and second separators 65 and 90 may e.g. be flash separators.

A hydrocarbon feed gas 1 is preheated in the preheating section 20 and becomes a preheated hydrocarbon feed gas 2, which is led to the purification unit 30. A purified preheated hydrocarbon feed gas 3 is sent from the purification unit 30 to the preheating section 20 for further heating. Moreover, steam 4 is added to the purified preheated hydrocarbon feed gas, resulting in feed gas 5 sent to a prereformer 40. Prereformed gas 6 exits the prereformer 40 and is heated in the preheating section 20, resulting in gas 7. In the embodiment of FIG. 1, hydrogen 14 is added to the gas 7, resulting in a feed gas 8 sent to the eSMR 50. The feed gas 8 undergoes steam methane reforming in the eSMR 50, resulting in a reformed gas 9 which is led from the eSMR 50 and from the reforming section 10 to the methanol section 60.

In the methanol section 60, the reformed gas 9 heats water 12 to steam 13 in a heat exchanger. In a first separator 85 water is separated from the synthesis gas 9 to provide a dry synthesis gas 11, which is sent to a compressor 70 arranged to compress the dry synthesis gas before it is mixed with recycle gas from a second separator 90 enters the methanol synthesis unit 80. Most of the produced methanol from the methanol synthesis unit 80 is condensed and separated in the second separator 90 and exits the methanol section as methanol 25. The gaseous component from the second separator 90 is split into a first part that is recycled to the methanol synthesis unit 80 and a second part that is recycled as an offgas 17 to be used as fuel 18 to the preheating section 20 of the reforming section 10 and/or recycled as feed 16 to the eSMR 50. An additional compressor is typically used for recycling the first part of the gaseous component from the second separator 95 to the methanol synthesis unit 80. Water 12 is heated to steam within heat exchangers of the system 100 and in the given embodiment inside the cooling side of the methanol synthesis unit 80.

In the case, where a second hydrocarbon feed gas is added to or mixed with the hydrocarbon feed gas upstream the reforming reactor, the second hydrocarbon feed gas is typically added to the hydrocarbon feed gas upstream the prereforming unit and the purification unit. In FIG. 1, this would correspond to adding the second hydrocarbon feed gas to the preheated hydrocarbon feed gas 2. The second hydrocarbon feed gas may be a stream of natural gas having a higher H/C ratio than the H/C ratio of the hydrocarbon feed gas of stream 1.

Such a system 100 according to the invention, comprising an electrically heated steam methane reformer and a methanol synthesis unit is also abbreviated eSMR-MeOH. Such an eSMR-MeOH system resembles a plant used in classical industrial process (SMR-MeOH) to a large extent, but deviates on some essential aspects. The use of the eSMR 50 removes the requirement for the intensive firing in the fired steam reformer of a classical SMR-MeOH system and thereby leaves only a small $CO_2$ emission from the eSMR-MeOH layout associated with purge gas handling. Moreover, in the case where the hydrocarbon feed gas is biogas, the use of biogas rather than natural gas as feedstock removes the requirement for oxygen addition to the synthesis gas as the natural high $CO_2$ content of biogas allows for the module adjustment inherently, as described below.

From an overall plant stoichiometry where methane (as natural gas) is used as feedstock, the reaction scheme can be expressed as:

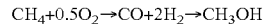

Alternatively, if a $CO_2$ feedstock is available, this can be used as oxygen source, giving an overall plant stoichiometry of:

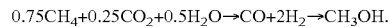

Higher temperatures can be reached in an eSMR compared with a fired reformer, which gives a better conversion of methane in this layout; in the end, this provides for less off-gas handling. It should be noted, that the $CO_2$ content in process gas can vary, and therefore, an addition $CO_2$ and/or CO, e.g. from the off-gas, to the synthesis gas can be advantageous.

The same methanol synthesis technology as in the classical approach can be used and the methanol reactor will in this layout have a $CO/CO_2$ ratio corresponding to that of a typical methanol plant and therefore have a similar activity and stability.

To some extent, at least part of the off-gas from the methanol synthesis unit can be recycled to the reforming section as feedstock to increase the carbon efficiency and recover unconverted methane. In the same way, it is also possible to recover the off-gas from a potential methanol distillation and return this as feedstock, if this is compressed to operating pressure. At least to some extent, preheating can be done by the excess steam, because high preheating. Electrically heated reforming can e.g. use a monolithic-type catalyst heated directly by Joule heating to supply the heat for the reaction. In its essence, the eSMR 50 is envisioned as a pressure shell having a centrally placed catalytic monolith, which is connected to an externally placed power supply by a conductor threaded through a dielectric fitting in the shell. The shell of the eSMR is refractory lined to confine the high-temperature zone to the center of the eSMR.

From a reforming reactor point of view, the eSMR has several advantages over a conventional fired reformer. One of the most apparent is the ability to make a significantly more compact reactor design when using electrically heated technology, as the reforming reactor no longer is confined to a system of high external heat transfer area. A size reduction of two orders of magnitudes is conceivable. This translates into a significantly lower capital investment of this technology. The combined preheating and reforming section of an eSMR (including power supply) configuration was estimated to have a significant lower capital investment. As the synthesis gas preparation section of a methanol plant accounts for more than 60% of the capital investment in a classical fired reformer based methanol plant, a drastic saving on the reformer equipment will translate into a significant reduction in the cost of a methanol plant based on eSMR.

Figure 2A:
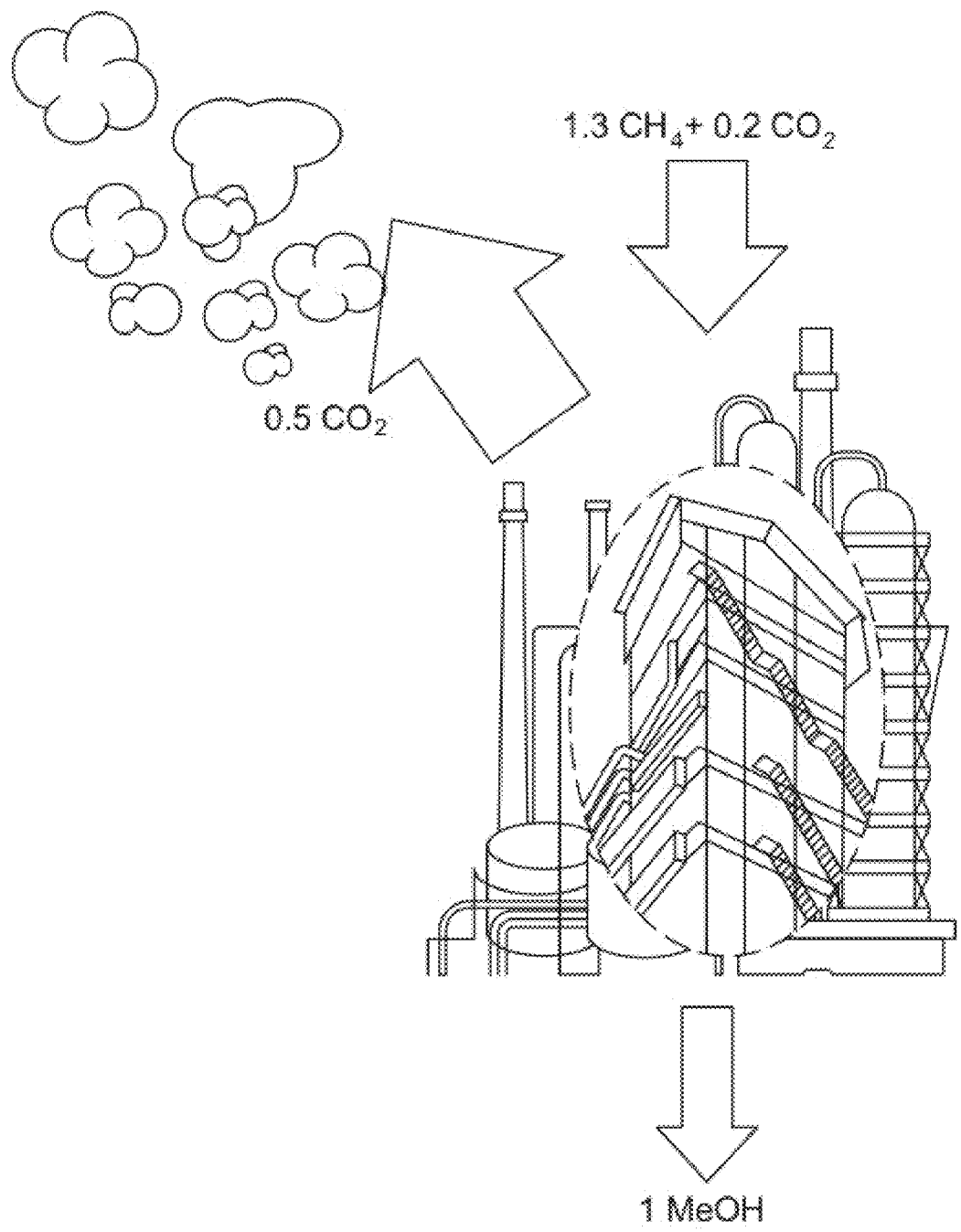
FIGS. 2a-2c show comparative cases for methanol plants based on a fired reformer versus an electric reformer versus alkaline electrolysis.
Figure 2B:
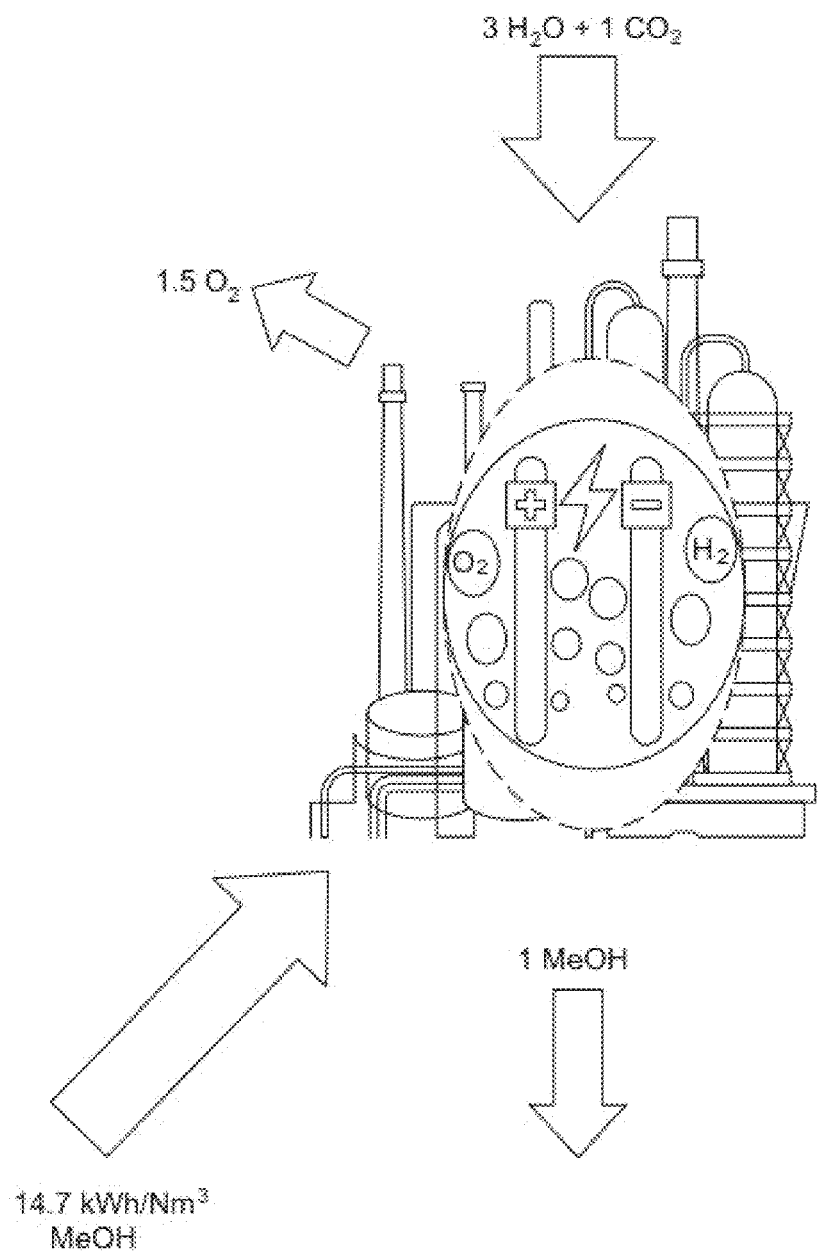
Figure 2C:
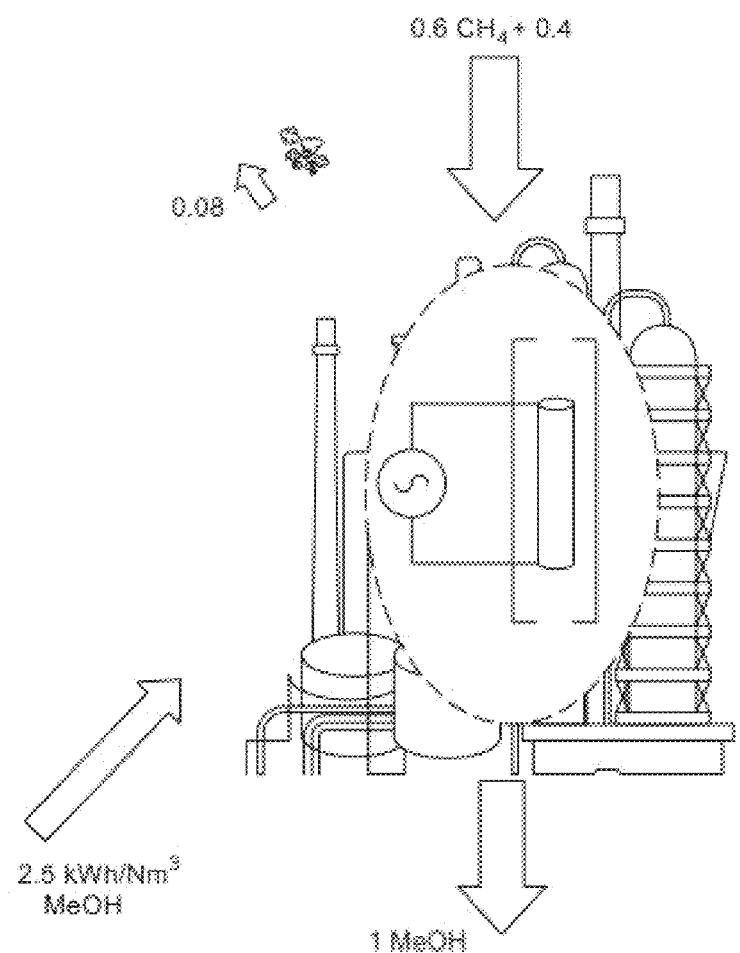

FIG. 2a-2c show comparative cases for methanol plants based on a fired reformer versus (FIG. 2a) an electric reformer (FIG. 2b) versus alkaline electrolysis (FIG. 2c). A major advantage of the eSMR of FIG. 2b is that it does not require burning hydrocarbons to provide the heat for the reaction, and consequently direct $CO_2$ emissions of this technology is significantly decreased. This is exemplified in FIGS. 2a-2c, showing how the consumables and $CO_2$ emissions can be markedly changed when using the eSMR-MeOH technology compared with both the fired reformer approach and electrolysis. The consumption figures of the fired reformer layout (FIG. 2a) and the eSMR-MeOH layout (FIG. 2b) are both based on Haldor Topsoe developed flowsheets for chemical-grade methanol production (i.e., including product distillation), while electrolysis layout (FIG. 2c) is an overall best-case stoichiometric analysis coupled with published consumption figures for alkaline electrolysis (AEL) based $H_2$ production and $CO_2$ purification. It should be noted, that the consumables are, from a chemical standpoint, divided in substantially pure $CH_4$ and $CO_2$ to not disadvantage the SMR-MeOH layout by requiring firing with hydrocarbon feed gas, which would have increased the $CO_2$ emissions from this plant considerably. In the given case, 30% reduction in methane consumption and 80% reduction in $CO_2$ emissions are achieved by the eSMR-MeOH compared to the fired reformer (SMR-MeOH). It is emphasized that process improvement may be considered for all presented cases, and should therefore not be considered limiting. When no units are given, the presented figures represent relative molar flow of components in FIG. 2a-2c.

The overview of the consumables of FIGS. 2a-2c illustrates a markedly lower electricity use for methanol production when using eSMR-MeOH over electrolysis. By use of SOEC instead of AEL in the electrolysis layout, the electricity use could potentially decrease to 11-13 $kWh/Nm^3$ MeOH (depending on availability of steam), which would be an improvement for this technology, but still markedly higher than eSMR-MeOH. Notice that the concept development still can be done on the electrolysis approach to improve the performance of this technology, but this is all at research stage and only established electrolysis technology, as AEL, combined with classical methanol synthesis technology can be considered ready for industrial application presently, why this is also the focus of the comparison.

Energy consumption of methanol production by AEL ("AEL-MeOH") is calculated as: $E_{total} = E_{AEL} + E_{CO_2} + E_{compress} - E_{steam}$. Here, $E_{AEL}$ is energy use of alkaline electrolysis with an energy efficiency of 71%. $E_{CO_2}$ is the energy use of $CO_2$ purification estimated as 2.6 $MJ/Nm^3$ $CO_2$ when using flue gas as feedstock. $E_{compress}$ is the compression power calculated at an efficiency of 75%, without including energy for cooling water, to be 0.7 $kWh/Nm^3$ Methanol. $E_{steam}$ is the potential energy recovery from steam production calculated as 75% recovery of the exothermic energy removed in the methanol synthesis estimated to be 0.7 $kWh/Nm^3$ Methanol. The calculation does not include any considerations on byproduct formation in the methanol synthesis unit or their integration in the plant layout.

Figure 3:
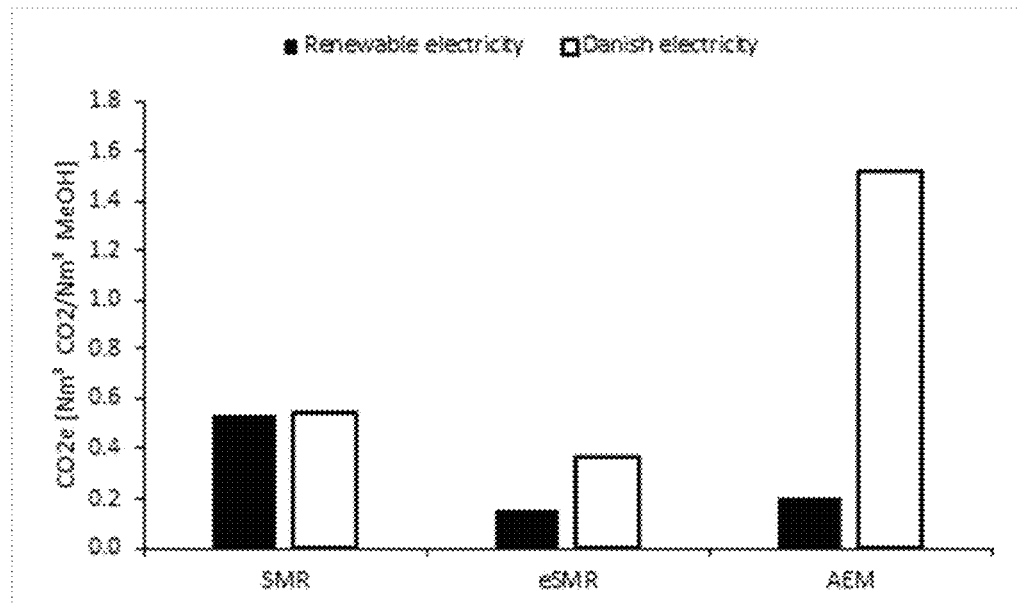
FIG. 3 shows $CO_2$ equivalent emissions ($CO_2$e) associated with production of MeOH as the combined contribution from: Plant emissions+Emissions from electricity generation.
Figure 4:
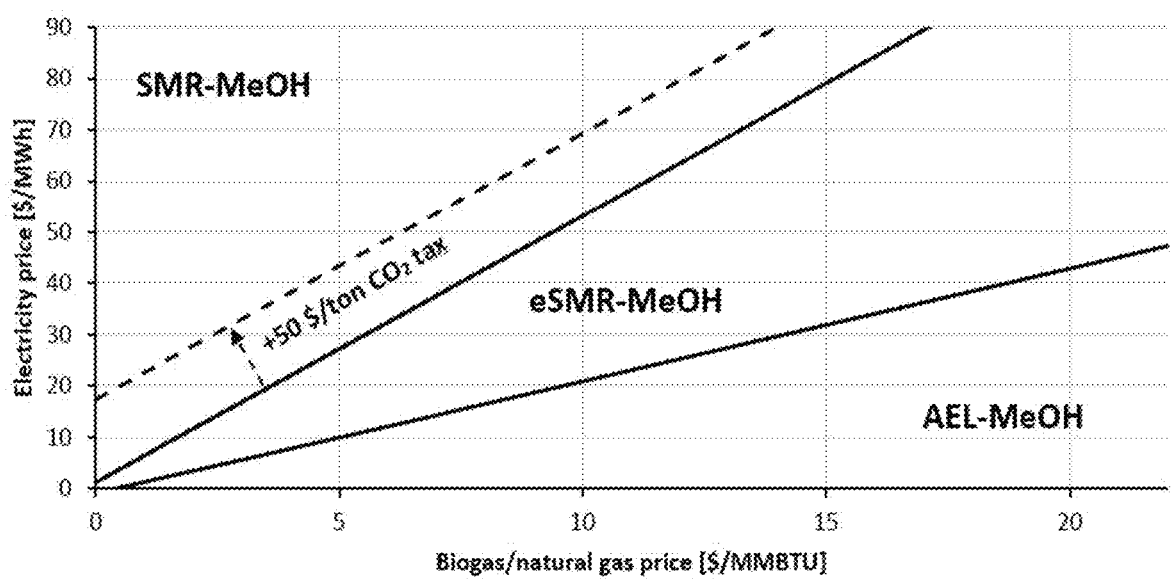
FIG. 4 is a graph of technologies with lowest operating expenses as a function of natural gas price and electricity price.

FIG. 3 shows $CO_2$ equivalent emissions ($CO_2e$) associated with production of methanol for SMR, eSMR and AEM, respectively. For each of these production technologies, the black box represent overall equivalent emissions ($CO_2e$) if the methanol was produced by renewable energy and the white box represent overall equivalent emissions ($CO_2e$) if the methanol was produced with electricity from the Danish electricity network in 2019. When calculating the overall $CO_2$ emissions from a chemical plant, the electricity consumption must be evaluated as well, as this could potentially also have a large $CO_2$ emission footprint. The exact emissions will be dependent on the source of the electricity. Looking at the associated equivalent $CO_2$ emissions ($CO_2e$) when electricity is provided either by fully sustainable resources or as an example the Danish energy grid in 2019, in which more than 60% of the annual electricity use is covered by sustainable sources as solar cells, wind power, and biomass. The actual $CO_2e$ for production of methanol by the eSMR-MeOH technology was on this basis calculated as shown in FIG. 3 and benchmarked against the conventional fired technologies and AEL-MeOH. Irrespective of the source of electricity, eSMR-MeOH will markedly better the $CO_2$ footprint of the methanol product over the conventional approach, viz. SMR-MeOH. While, based on the energy grid in Denmark in 2019, the electrolysis approach will not have a positive effect on the $CO_2e$. Only when the electricity is fully renewable, the electrolysis approach will have an $CO_2e$ comparable to the eSMR-MeOH route, but AEL-MeOH will still be 35% higher FIG. 4 is an overview of technologies with lowest operating expenses as a function of natural gas price and electricity price.

To make sustainable technology attractive, it must be cost-competitive compared to the established production routes. FIG. 4 shows an overview of which technology gives the lowest operating expenses as a function of gas and electricity price. It should be noted, that the overview only shows operating expenses. If expenses to plant depreciation is included in the production costs, the size of the area indicated "eSMR-MeOH" would markedly increase into the areas denoted "AEL-MeOH" and "SMR-MeOH", because the eSMR-MeOH technology has a significantly lower capital investment compared with the two other technologies. From this overview it can be seen that the fired technology (SMR-MeOH) has been the cheapest production route for the last century because it is favoured by the low gas prices. However, the decreasing electricity prices opens for an incentive toward the electrically driven technologies. An eSMR driven frontend is proposed as a next step for a cost-competitive route for methanol production. To exemplify the opportunity, competitive cases can be found when comparing with natural gas prices of ca. 6-8 $/MMBTU in Europe. The operating expenses of the eSMR-MeOH technology will be further favoured in cases with $CO_2$ taxation, which will increase the operating expenses of the fired reformer approach significantly. This is indicated by the dashed line in FIG. 4, with a representative $CO_2$ tax of the Nordic countries today. It is emphasized that FIG. 4 is only indicative, as the development within the eSMR-MeOH layout is still in a relatively early phase. It is foreseen that development within eSMR-MeOH will improve the consumption figures further, and thereby the operating expenses.

While the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative methods, and illustrative examples shown and described. Accordingly, departures may be made from such details without departing from the spirit or scope of applicant's general inventive concept.

Example 1

Example 1 relates to an embodiment of the invention where a biogas is converted into methanol, cf. FIG. 1 for reference. A feed gas (1) is mixed with a $CO_2$ feed to adjust the synthesis gas module and a recycle gas from a methanol loop to provide hydrogen for the subsequent desulfurization (30) and prereforming (40) steps. Using an electrically heated reformer (50), the gas is converted with steam (4) into a synthesis gas. This is cooled and separated into a condensate and dry synthesis gas (11), where the dry synthesis gas is compressed and fed to a methanol loop using a boiling water type methanol reactor (80). The compressed make-up synthesis gas is mixed with recycled gas (95) in the loop and sent to the methanol reactor (80) to produce methanol. By cooling and condensing this methanol is separated to produce the final product (25). Most of the off-gasses from this separation are recycled (95) directly to the methanol reactor, another fraction (16) is recycled to the feed, while the last fraction is exported as a fuel rich off-gas.

Overall, this embodiment of the process allows for converting 95.4% of the carbon feedstock ($CO_2$+$CH_4$) into methanol.

| Example 1 | | | | | | | |
|---|---|---|---|---|---|---|---|
| | Feed (1) | Feed addition | Off-gas recycle | Inlet desulfurization (2) | Inlet prereformer (5) | Inlet reformer (8) | Outlet reformer |
| T [° C.] | 179 | 164 | 40 | 380 | 27 | 26.3 | 1050 |
| P [barg] | 30 | 31 | 85.5 | 29.5 | 293 | 343 | 25.3 |
| Components [Nm³/h] | | | | | | | |
| $CH_3OH$ | 0 | 0 | 3 | 3 | 3 | 0 | 0 |
| $CH_4$ | 1863 | 0 | 71 | 1933 | 1933 | 1997 | 113 |
| CO | 0 | 0 | 27 | 27 | 100 | 1 | 2208 |
| $CO_2$ | 1 | 626 | 24 | 651 | 580 | 617 | 294 |
| $H_2$ | 0 | 0 | 322 | 322 | 240 | 93 | 5421 |
| $N_2$ | 5 | 0 | 13 | 18 | 18 | 18 | 18 |
| $O_2$ | 5 | 0 | 0 | 5 | 1 | 0 | 0 |
| $H_2O$ | 0 | 0 | 0 | 0 | 2898 | 2926 | 1365 |

| | Outlet flash separator (11) | Outlet make-up-gas compressor | After recycle mixing and inlet MeOH reactor | Outlet MeOH reactor | Outlet recycle compressor | MeOH Product (25) |
|---|---|---|---|---|---|---|
| T [° C.] | 40 | 123 | 220 | 260 | 46 | 40 |
| P [barg] | 23.9 | 90 | 90 | 87 | 90 | 90 |
| Components [Nm³/h] | | | | | | |
| $CH_3OH$ | 0 | 0 | 92 | 2468 | 92 | 2376 |
| $CH_4$ | 113 | 113 | 2659 | 2659 | 2547 | 92 |
| CO | 2208 | 2203 | 3169 | 1005 | 966 | 39 |
| $CO_2$ | 293 | 293 | 1177 | 966 | 885 | 81 |
| $H_2$ | 5420 | 5409 | 17081 | 12116 | 11670 | 446 |
| $N_2$ | 18 | 18 | 471 | 471 | 453 | 18 |
| $O_2$ | 0 | 0 | 0 | 0 | 0 | 0 |
| $H_2O$ | 24 | 14 | 17 | 229 | 3 | 226 |

| | Off-gas recycle | Off-gas |
|---|---|---|
| T [° C.] | 40 | 40 |
| P [barg] | 85.5 | 85.5 |
| Components [Nm³/h] | | |
| $CH_3OH$ | 3 | 0 |
| $CH_4$ | 71 | 21 |
| CO | 27 | 8 |
| $CO_2$ | 24 | 8 |
| $H_2$ | 322 | 103 |
| $N_2$ | 13 | 3 |
| $O_2$ | 0 | 0 |
| $H_2O$ | 0 | 0 |

The invention claimed is:

1. A method for upgrading a hydrocarbon feed gas to methanol, comprising the steps of:
   a1) providing a hydrocarbon feed gas,
   b1) optionally, providing $CO_2$ to the process,
   b2) optionally, purifying the hydrocarbon feed gas in a gas purification unit,
   b3) optionally, prereforming the hydrocarbon feed gas together with a steam feedstock in a prereforming unit,
   c) carrying out steam methane reforming in a reforming reactor comprising a pressure shell housing a structured catalyst arranged to catalyze steam reforming of said hydrocarbon feed gas, said structured catalyst comprising a macroscopic structure of an electrically conductive material, said macroscopic structure supporting a ceramic coating, where said ceramic coating supports a catalytically active material; said steam methane reforming comprising the following steps:
   c1) supplying said hydrocarbon feed gas to the reforming reactor,
   c2) allowing the hydrocarbon feed gas to undergo steam methane reforming reaction over the structured catalyst and outletting a synthesis gas from the reforming reactor, and
   c3) supplying electrical power via electrical conductors connecting an electrical power supply placed outside said pressure shell to said structured catalyst, allowing an electrical current to run through said macroscopic structure material, thereby heating at least part of the structured catalyst to a temperature of at least 500° C.,
   d) providing at least part of the synthesis gas from step c2) to a methanol synthesis unit to provide a product comprising methanol and an off-gas.

2. The method according to claim 1, wherein the electrical power supplied is generated by means of renewable energy sources.

3. The method according to claim 1, wherein an electrolysis unit is used to generate a hydrogen rich stream from a water feedstock and where said hydrogen rich stream is added to the synthesis gas to balance the module of said synthesis gas to be in the range of 1.5 to 2.5.

4. The method according to claim 3, wherein the electrolysis unit is a solid oxide electrolysis cell unit and said water feedstock is in the form of steam produced from other processes of the method.

5. The method according to claim 1, wherein a membrane unit is included in the methanol synthesis unit to extract at least a part of the carbon containing molecules from said off-gas and return said at least part of the carbon containing molecules from said off-gas to the synthesis gas to balance the module of the synthesis gas to be in the range of 1.5 to 2.5.

6. The method according to claim 1, wherein a combination of steam superheating and steam generation is integrated in waste heat recovery of said synthesis gas from the reforming reactor, and wherein the superheated steam is used as steam feedstock in step c) of the method for upgrading a hydrocarbon feed gas to methanol.

7. The method according to claim 1, wherein the pressure of the gas inside said reforming reactor is between 20 and 100 bar.

8. The method according to claim 1, wherein the temperature of the gas exiting said reforming reactor is between 90° and 1150° C.

9. The method according to claim 1, wherein the space velocity evaluated as flow of gas relative to the geometric surface area of the structured catalyst is between 0.6 and 60 $Nm^2/m^2/h$ and/or wherein the flow of gas relative to the occupied volume of the structured catalyst is between 700 $Nm^3/m^3/h$ and 70000 $Nm^3/m^3/h$.

10. The method according to claim 1, wherein the plot area of said reforming reactor is between 0.4 $m^2$ and 4 $m^2$.

11. The method according to claim 1, wherein the production of methanol is regulated according to availability of renewable energy.

12. The method according to claim 1, wherein the method further comprises the step of upgrading the methanol to fuel grade methanol.

13. The method according to claim 1, wherein the method further comprises the step of upgrading the methanol to chemical grade methanol.

14. The method according to claim 1, wherein the method further comprises the step of using at least part of the methanol of step d) to a system for producing transportation fuel.

15. The method according to claim 1, wherein at least part of the off-gas is recycled to upstream the reforming reactor.

16. The method according to claim 1, wherein between 80% and 100% of the carbon in the hydrocarbon feed gas is converted into methanol.

17. The method according to claim 1, wherein the hydrocarbon feed gas amounts to 500 $Nm^3/h$ to 8000 $Nm^3/h$.

18. A system for upgrading hydrocarbon feed gas to methanol, comprising:
   an optional gas purification unit,
   an optional prereforming unit,
   a reforming reactor comprising a pressure shell housing a structured catalyst arranged to catalyze steam reforming of a feed gas comprising hydrocarbons, said structured catalyst comprising a macroscopic structure of an electrically conductive material, said macroscopic structure supporting a ceramic coating, where said ceramic coating supports a catalytically active material; wherein the reforming reactor moreover comprises an electrical power supply placed outside said pressure shell and electrical conductors connecting said electrical power supply to said structured catalyst, allowing an electrical current to run through said macroscopic structure material to thereby heat at least part of the structured catalyst to a temperature of at least 500° C.,
   a methanol synthesis unit arranged to receive at least part of the synthesis gas from said reforming reactor and produce a product comprising methanol and an off-gas.

19. The system according to claim 18, wherein catalyst pellets are loaded on top of, around, inside, or below the structured catalyst of the reforming reactor.

* * * * *